Figures 3, 4:
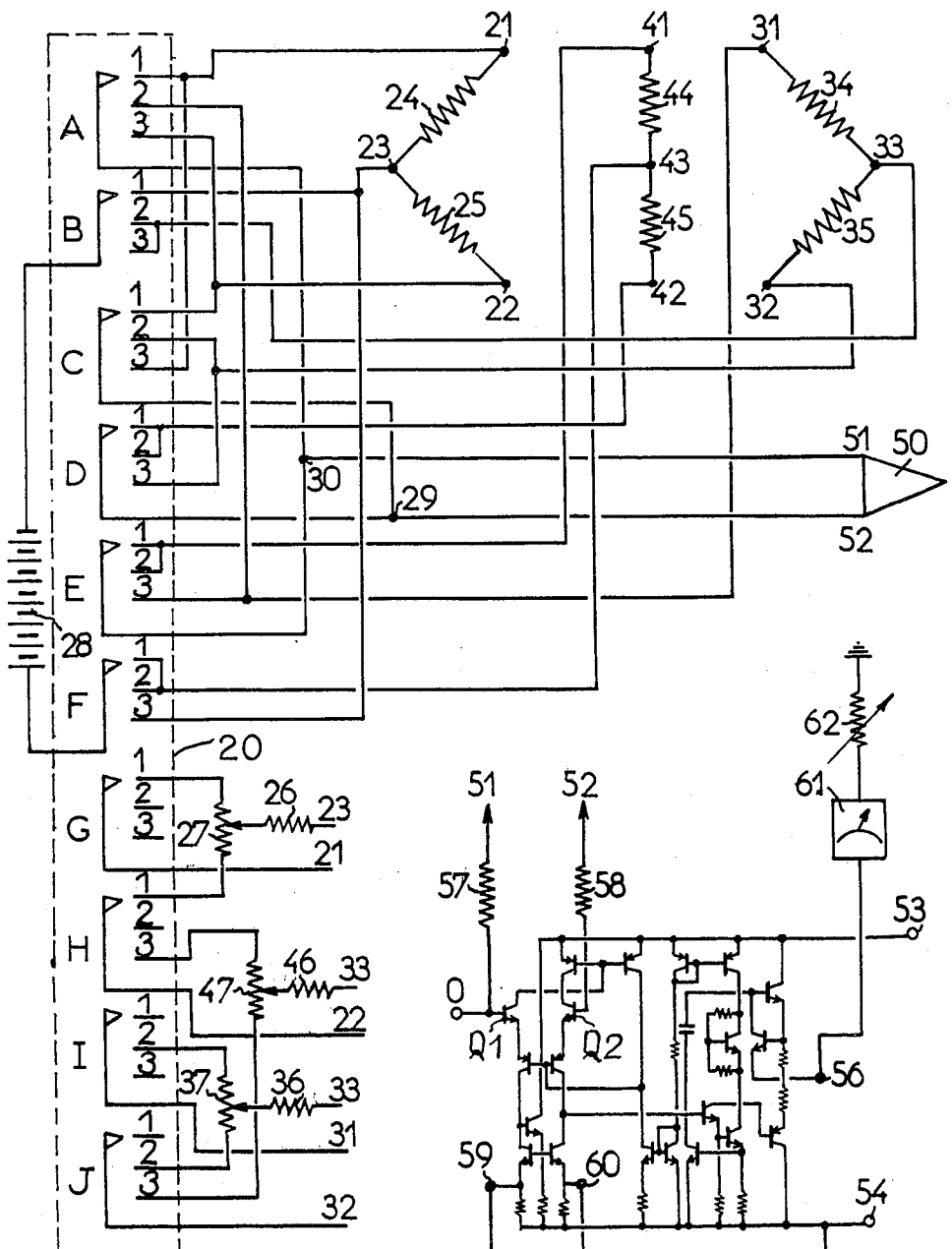

United States Patent [19]

Blanque

[11] 3,996,666
[45] Dec. 14, 1976

[54] DEVICE FOR CONTINUOUS AUSCULTATION OF THE MOTION AND POSITIONS OF A PATIENT MANDIBLE

[76] Inventor: Pierre Blanque, 5, Ave. des Montagnes, 64200 Biarritz, France

[22] Filed: Dec. 17, 1974

[21] Appl. No.: 533,538

[30] Foreign Application Priority Data

Dec. 17, 1973 France .............................. 73.44976

[52] U.S. Cl. .................................. 32/19; 128/2 S
[51] Int. Cl.² .......................................... A61C 9/00
[58] Field of Search .................. 32/19, 32; 128/2 S, 128/2 N, 2 R; 33/174 D

[56] References Cited

UNITED STATES PATENTS

| | | | |
|---|---|---|---|
| 3,256,523 | 6/1966 | De Pietro | 32/19 X |
| 3,259,984 | 7/1966 | Seidenberg | 32/32 |
| 3,307,262 | 3/1967 | Chaiken | 32/19 |
| 3,382,581 | 5/1968 | Balazs | 32/19 |
| 3,614,950 | 10/1971 | Rabey | 128/2 S |
| 3,643,332 | 2/1972 | Lee | 32/19 |
| 3,651,577 | 3/1972 | Brenman | 32/19 |
| 3,822,694 | 7/1974 | Mills | 32/19 X |

*Primary Examiner*—Robert Peshock
*Assistant Examiner*—Jack Q. Lever
*Attorney, Agent, or Firm*—Daniel M. Rosen; Yuter & Rosen

[57] ABSTRACT

Device for continuous auscultation of the motion and positions of a patient mandible including means for sensing the motion and positions of the mandible at the rear of the condyle inside the external auditory duct with the help of strain gauges connected with a Wheatstone bridge, and means for amplifying the output signal which is finally applied to a reading device. Such a device is usable for real and accurate determination of any mandibular motion, centric relation and rest position in making dental prosthesis.

14 Claims, 4 Drawing Figures

U.S. Patent  Dec. 14, 1976  Sheet 1 of 2  3,996,666
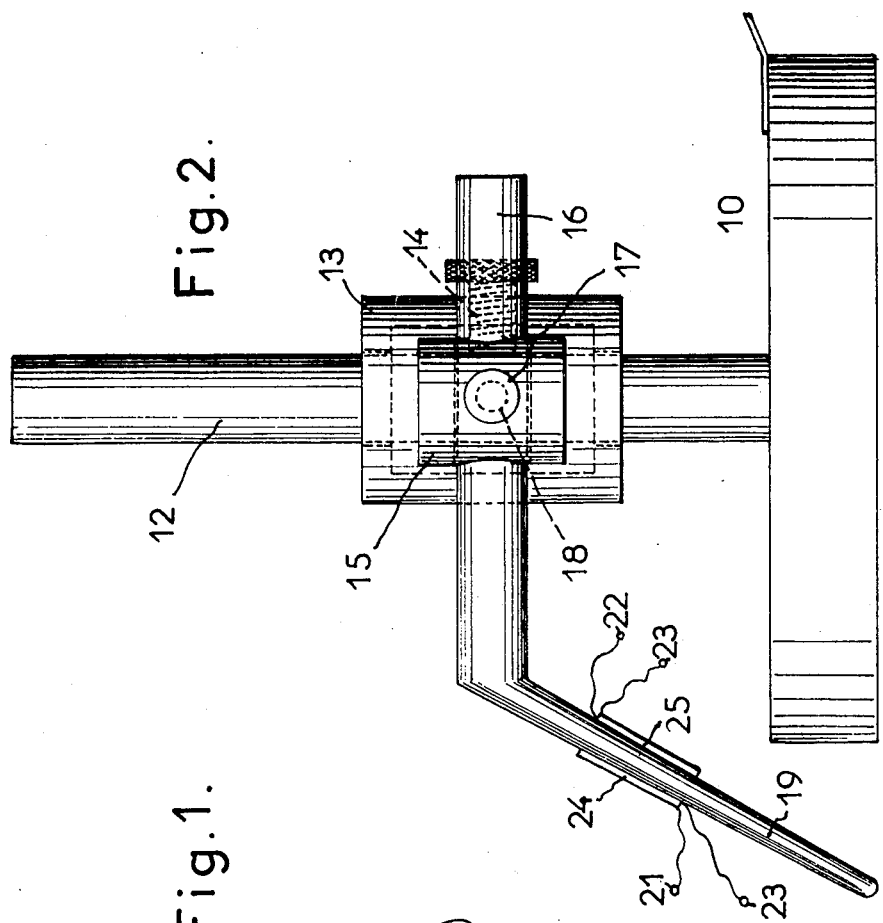
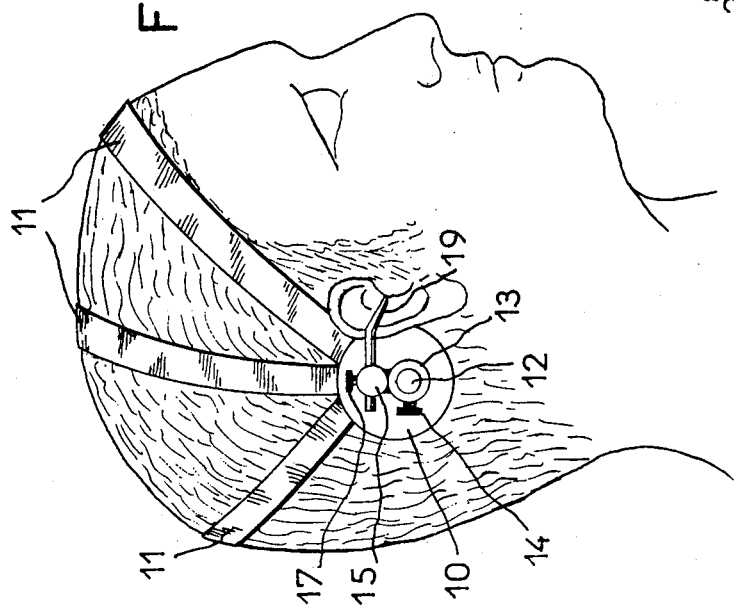

DEVICE FOR CONTINUOUS AUSCULTATION OF THE MOTION AND POSITIONS OF A PATIENT MANDIBLE

THE INVENTION

The present invention relates to a device serving for permanent auscultation of the mandibular movements of a patient. It is particularly intended for externalizing the position of the mandible at all stages of prosthetic restoration, for example.

It is known in particular that in the case of a complete dental prosthesis it is important to obtain proper positioning of the mandible at the time of the consecutive phases of taking imprints. This taking of imprints is normally followed by the placing in the mouth of occulusion models, from which will be finally determined the centered relationship of the mandible with regard to the maxillaries so that, in the final phase of occlusion, the prostheses may engage under optimal physiological conditions.

It is in fact known that the occlusion models must prefigure the finished prosthesis. Perfect placement is therefore essential. The major difficulty resides in finding an occlusion in a centered relation, that is, according to the definition given by the American specialist Carl O. Boucher, in the relation existing between the mandible and the upper maxillary, at a correct vertical occlusion dimension, when the condyles are situated in their rearmost position, without constraint, in the glenoid cavity, a position from which lateral movements and a slight movement of retroversion are possible.

Now, the principal difficulty in obtaining a correct centered relation comes from the fact that when the patient is fitted with occlusion models he commits essentially two principal errors which are essentially errors in appreciation at the time of closing the jaws which are reflected by either mandibular propulsion or mandibular lateral deviation. Another major difficulty which arises is the determination of the vertical dimension in the physiological state of rest. This represents one of the most difficult elements to determine in the dental art.

With regard to the determination of this vertical dimension, various methods have been used in the previous art based on the existence or absence of pre-extraction documents. In the event that such documents exist, the most current method resides in the use of profile photographs or teleradiography allowing the angle formed between the Frankfort plane and the basilar edge of the mandible to be determined. This method proves to be very imprecise. Another method used consists of prior tattooing before any extraction, allowing the distance between the upper maxillary and lower maxillary to be determined. This distance is noted on a card. However, it leads to a certain imprecision: in point of fact, after the extractions, there can occur resorption of the alveolar bone which alters the relative distances of the pre-established markings.

In the absence of pre-extraction documents, various methods are based either on restoration of the patient's esthetic or on other relationships existing among characteristic points of the face (Wright's technique or Willis' technique). It would be tiresome, within the framework of the present invention, to enumerate them entirely.

These methods have proved imprecise and difficult to materialize in the presence of the patient. Among all of them, the most interesting has shown itself to be the seeking of the patient's tactile sense and the sensation of comfort felt when the muscular tone of the lowering and elevating muscles becomes balanced: this in fact constitutes an ideal means of determining the vertical dimension sought. However, in the dentist's office, in the presence of the practitioner, the patient experiences difficulties in externalizing his sensation of comfort owing to the muscular contraction which results from a certain degree of emotionality and/or apprehension felt.

As regards the methods used until now to determine the centered relation, the previous art made use of methods based on graphic recording of the position of the mandible. The most simple device was composed of a recording stylus affixed to the anterior face of the upper pad in the median sagittal axis in such a way that its end was on the plane of occlusion. A recording plate was affixed to the anterior face of the lower pad in its median position in such a way that its upper surface was in the prolongation of the occlusive surface of the pad. The major drawback to this method was the emcumbrances in the oral-buccal sphere of the patient, reflected by an increase in his awkwardness in seeking the optimal occlusion position.

A dental device to determine the natural occlusion at the time of prosthesis is known from U.S. Pat. No. 3,382,581. But on the one hand the pickup rests on the patient's cheekbone which diminishes the sensitivity of the device as a result either of parasitic indications such as ties or blood pulsations or of the thickness of the integuments (adipose subjects), and on the other hand the indication is discontinuous (extinguishing or lighting of a pickup).

In addition, this patent gives no indication of combining a pickup with means for amplification and detection of the signal picked up, and with means for continuously reading the same signal.

Lastly, the device described causes an emcumbering of the oral-buccal sphere, which on the one hand hampers the dentist and on the other hand prevents the patient from being relaxed and makes him awkward in seeking the optimal occlusion position in case of total prosthesis. Other devices are described in U.S. Pat. Nos. 3,256,523 and 3,259,984 which have the same drawback of having measuring devices directly linked to the teeth in an intrabuccal manner.

The present invention has for its purpose to eliminate the disadvantages encountered with the application of the methods of the previous art and to permit the production of a device allowing permanent auscultation of a patient's mandibular movements, without presenting the slightest discomfort for him. The present invention is based on the fundamental observation that all movement of the mandible is reflected by a displacement of the condyle. These variations in the position of the condyle are easy to perceive at the level of the external auditory meatus, a phenomenon which, by the way, can be fairly readily verified by palpation at the aforesaid level. This observation, which has never been the object of any industrial exploitation until the present, has led to the designing of a device containing a displacement pickup which can be introduced on the appropriate part of the external auditory meatus, resting on the posterior part of the condyle.

According to a characteristic of the invention, the device comprises in combination: a means of picking up pressure and/or displacement which can be applied at the level for the external auditory meatus, and which can enternalize the variations in the position of the condyle, a means of locking said pickup onto a fixed support connected to the patient, means for detection and amplification of the signal picked up and means for reading the indications which reflect the variations in current corresponding to the various positions of the condyle.

According to a particular design, the pressure pickup is composed of at least a couple of gauges of extensiometry, each of which constitutes the resistance of a Wheatstone bridge. The variations in balance of the bridge are noted by a means for reading such as a galvanometer needle, graphic recorder or cathode ray tube.

The invention will be better understood in relation to the figures annexed, which represent:

FIG. 1, the mode of installation of the movement pickup on the patient's head.

FIG. 2, the details of the composition of the movement pickup.

FIG. 3, the detailed mode of design of the circuit of detection and amplification of information emanating from the movement pickup.

FIG. 4, the detailed amplification circuit.

According to a mode of design of the invention represented by FIGS. 1 and 2, the device comprises two braces 10 intended for affixing to the patient's head by fastenings 11 connecting the two bases. These fastenings are advantageously composed of adjustable straps or metallic elements the elasticity whereof permits the placing and affixing thereof to the patient's skull, so as to prevent any relative movement between the base 10 and the patient's head. According to another mode of design, the fastenings 11 can be replaced by a rigid helmet widely recessed at the location of the auricular canal. On the base 10 is mounted a cylindrical axis 12 on which slides, with low friction, an annular sleeve 13 capable of turning around the axis 12. A threaded recess 14 allows a screw, not shown, to block the travel and rotation of the sleeve 13. Locked onto the sleeve 13, a cylindrical sleeve 15 exhibits a cylindrical recess wherein there may slide perpendicularly to the axis 12 a rod 16 which can be blocked in its travel and rotation by the screw 17 turning in the threads 18 of sleeve 15.

Even though, for convenience in the drawing, the blocking device has been represented by a screw 17, any other known means can be used. For example, in another mode of design, the screw 17 has been replaced by a rack system allowing precise adjustment of the movement of the rod 16 in its anterioposterior motion in relation to the patient's auditory canal. The rod 16 bears at its end an elbow-shaped part 19, articulated by means of a pullback spring not shown so as to ensure permanent contact on the posterior part of the condyle in order to measure all its movements. In a preferred mode of design, the rod 19 is composed of an elastic blade itself forming a spring so as to rest on the posterior part of the condyle. On two flat pieces diametrically opposite each rod 19 are mounted two extensiometric gauges of known type, said active gauges respectively 24 and 25 for the rod 19 situated on the patient's left and 34 and 35 for rod 19 on his right. The active gauges 24 and 25 comprise connections ending respectively at terminals 21, 23 and 22, 23, as shown in FIG. 2.

FIG. 3 shows how these active gauges are connected to the measuring device.

A commutator 20 has 10 contacts A, B, C, D, E, F, G, H, I, J which can each occupy one of the 3 positions 1, 2 and 3.

The active gauges 24 and 25 have a common point 23 connected on one side to the stud $B_1$ and on the other to the stud $F_3$ of the commutator 20. The other terminal 21 of gauge 24 is connected to studs $A_1$ and $C_3$ while terminal 22 of gauge 25 is connected to studs $A_3$ and $C_1$.

The point 33 common to gauges 34 and 35 communicates with studs $B_2$ $B_3$. Terminal 31 of gauge 34 is connected to studs $A_2$ and $E_3$ while terminal 32 of gauge 35 communicates with the studs $C_2$ and $D_3$.

A couple of inert gauges 44 and 45 has a middle point 43 connected to studs $F_1$ and $F_2$ while terminal 31 of 34 communicates with studs $A_2$ and $E_3$ and the terminal 32 of 35 is connected with studs $C_2$ and $D_3$.

Between the runners B and F is connected a source 28 of 6 volt direct current.

It is readily observable from FIG. 3 that when the commutator is on position 1 the active gauges 24 and 25 constitute, with the inert gauges 44 and 45, a first Wheatstone bridge following the circuit 21 - Al - 30 - $E_1$ - 41 - 44 - 43 - 45 - 42 - $D_1$ - 29 - $C_1$ - 22 - 25 - 23 - 24 and 21. The bridge is powered between terminals 23 and 43 by the battery 28 while the measuring current received respectively at 29 and 30 is applied to the terminals 51 and 52 of a differential amplifier 50, described below.

It can similarly be verified that on position 2 of commutator 20 a second Wheatstone bridge is constituted by the 2 active gauges 34 and 35 and the 2 inert gauges 44 and 45, while on position 3 of the commutator 20 a third bridge is constituted by the group of active gauges 24, 25, 34 and 35.

Studs G, H, I, J of the commutator 20 serve to balance the 3 Wheatstone bridges mentioned above.

On position 1 of the commutator 20 the circuit constituted by terminal 21, stud $G_1$, the resistance 27 and stud $H_1$ and the terminal 22 is connected between the 2 active gauges 24 and 25.

The balancing of the first bridge is effected by modifying on the resistance 27 of 50 $k\omega$ the position of the runner connected to the resistance 26 of 30 $k\omega$ the other end whereof is connected to the terminal 23.

On position 2 of the commutator 20, the balancing circuit is constituted by terminal 31, stud $I_2$, the resistance 37 of 50 $k\omega$ the runner whereof is connected through the resistance 36 to the terminal 33, the stud $J_2$ and the terminal 32.

On position 3 of the commutator 20, the balancing circuit is constituted by the terminal 22, the stud $H_3$, the resistance 47 the runner whereof is connected through the resistance 46 connected to the terminal 33 the stud $J_3$ and the terminal 32.

In the device which has just been described, 2 active gauges have been mounted on each of the rods 19 to obtain more sensitivity. It is of course understood that a simpler installation can be made by utilizing only a single couple of active gauges 24 and 34, for example. In this case, the gauges 25 and 35 are replaced in the bridge by simple resistances analogous to the inert gauges 44 and 45.

FIG. 4 shows the drawing of an operational amplifier which can be used to amplify the signals reflecting the imbalance of the Wheatstone bridge engendered by variations in resistance of one of the active gauges. Such a scheme is sufficiently classic to enable an informed technician to produce the device. As it does not constitute the principal means of the invention, its detailed description is not required. Such operational amplifiers are well known: we may mention among them as an example the amplifier type SF. C 2741 M marketed by the French firm SESCOSEM and which is presented in the form of an integrated circuit.

The power supply of the amplifier 50 is provided by applying a direct current of + 6 volts on the terminal 53 and − 6 volts on the terminal 54. The signal coming from one of the Wheatstone bridges in operation is applied to the terminals 51 and 52 and connected to the bases of input transistors $Q_1$ and $Q_2$ through resistances 57 and 58 respectively of 1 $k\omega$, while the output signal is taken at 56 to be transmitted to a measuring or recording device here represented in the form of the galvanometer 61 grounded by an adjustable potentiometer 62.

A potentiometer 55 connected between the terminals 59 and 60, the runner whereof is connected to the direct negative voltage terminal 54 and serves for the balancing of the amplifier 50.

Between the terminals 54 and 56 there can be connected, if need be, a sensitivity commutator, not shown for clarity in the figure, which, by interposing a set of resistances of different values between the input and output of the amplifier, permits different amplifier sensitivities to be obtained.

In place of the galvanometer 61 or in parallel thereon there can be mounted, as needed, other means of reading, in particular a graphic recorder, a cathode ray tube or a magnetic recording device. The functioning of the device operates as follows. The practitioner affixes the base 10 by means of the fastenings 11 or by any other means so as to ensure perfect immobility of the base 10 in relation to a fixed point on the patient's head, preferably at the level of the mastoidal area. The active and inert gauges are then connected as indicated in FIG. 3 and the runners of the potentiometers 27, 37 and 47 are successively adjusted — the commutator 20 being respectively on positions 1, 2 and 3 — to a predetermined position allowing sufficient play of the indicating apparatus, which is preferably at central zero.

One then acts on the sensitivity commutator connected between 52 and 56 in such a way that the value of the counter-reaction resistance introduced gives the desired sensitivity to measure the movements of the condyle. The impedance 62 of the galvanometer 61 is then adjusted in such a way as to obtain a desired amplitude deviation.

Once the various preliminary adjustments have been made, the device is actually in operating order and the least variation in the condyle's position is reflected by an ohmic variation of the couple of active left or right gauges considered, which produces a signal amplified by the amplifier 50 and reflected on the means of reading 61.

The use of the device is performed in the following manner. The first position to be sought is the physiological position of rest. The patient being in a relaxed position, the practitioner determines on the galvanometer, for example, the needle position. This exercise is repeated several times, in such a way as to ensure that the needle always returns to the same position which corresponds to the natural position of rest of the patient's mandible, the commutator 20 being placed successively on positions 1, 2 and 3. At that time, the practitioner places in the mouth first the upper occlusion model, then reverifies the physiological position of rest, the upper model being in place. He has his patient perform deglutition exercises which enable him to pick up the personal kinematics of his patient's mandible by reading the galvanometer needle or, even better, the graphic recording. He then places the lower occlusion model and then determines the vertical occlusion dimension in function of the prior indication of the vertical physiological dimension of rest. Then, asking his patient to bite into the occlusion pads, he determines the occlusion in the centered relation, which is the purpose of the operation. This delicate operation is then the subject of several verifications by a repetition of the movements of closing and opening. Any unfavorable movement, propulsion or lateral deviation, is immediately detected by an action on the extensiometric gauges which produces an abnormal movement of the galvanometer needle in relation to the movement previously determined on the reading device. Once the occlusion in the centered relation is determined, the upper and lower occlusion models are locked together and withdrawn from the patient's mouth. Propulsive and lateral movements can be the subject of classic graphic recordings on models for purposes of checking. It is thus seen that the invention, in a simple manner for the practitioner as it is reflected by a simple reading, very slight for the patient and without any discomfort, makes possible the continuous determination of the physiological position of rest, and also of all mandibular movements of closure, propulsion and lateral deviation of the patient.

I claim:
1. A device for permanent auscultation of the mandibular movements of a patient of the type structured to penetrate into the external auditory meatus and to be applied onto the posterior part of the condyle, comprising means for sensing the displacement of the condyle through the external auditory meatus resulting from mandibular movements and providing a signal representative of said displacement, means for detection and amplification of said signal corresponding to said displacement, and means for indicating the variations of said signals and corresponding to the various movements and positions of the condyle.
2. Auscultation device according to claim 1 wherein said pressure pickup is composed of at least two extensiometric gauges, locked respectively onto restraining pieces applied directly to the condyle.
3. Auscultation device according to claim 1 wherein said means for detection include a Wheatstone bridge formed by said two extensiometric gauges applied on one of the patient's condyles and a set of inert gauges.
4. Auscultation device according to claim 1 wherein said means for detection include a Wheatstone bridge formed by said two extensiometric gauges respectively applied to each of the patient's two condyles.
5. Auscultation device according to claim 1 wherein said means for indicating is a galvanometer.
6. Auscultation device according to claim 1 wherein said means for indicating is a graphic recorder.
7. Auscultation device according to claim 1 wherein said means for indicating is a cathode ray tube.
8. Auscultation device according to claim 1 wherein said means for indicating is a magnetic tape recording device.
9. Device according to claim 1 wherein said means for sensing is applied onto the patient's head by a helmet providing fixed mastoidal support.

10. A device for providing signal indications corresponding to mandibular movements of a patient, comprising means adapted to be bound at one end to the patient's skull and at the other end in close contact with the condyle of said patient, said means including a sensing element in close contact on the posterior part of said condyle in the external auditory meatus of the patient, first means coupled to said element for sensing the movement of said element resulting from a range of mandibular movement causing a corresponding condyle movement, means for detection coupled to said means for sensing for providing a signal representative of said movement, and means for indicating said signal coupled to said means for detection.

11. The device of claim 10 wherein said element is elastic and said means for sensing includes a couple of extensiometric gauges.

12. The device of claim 11 wherein said means for detection includes a second couple of resistive elements forming, together with said couple of extensiometric gauges, a Wheatstone bridge.

13. The device of claim 10 further including a second sensing element adapted for contact on the posterior part of the condyle in the other external auditory meatus of the patient, and second means coupled to said second sensing element for sensing the movement of said second sensing element.

14. The device of claim 13 wherein a multiposition switch couples said first means and said second means, alternatively or simultaneously, to said means for detection.

* * * * *